Jan. 1, 1957 E. S. BOERNER Plant Pat. 1,547
CHRYSANTHEMUM PLANT
Filed Feb. 27, 1956
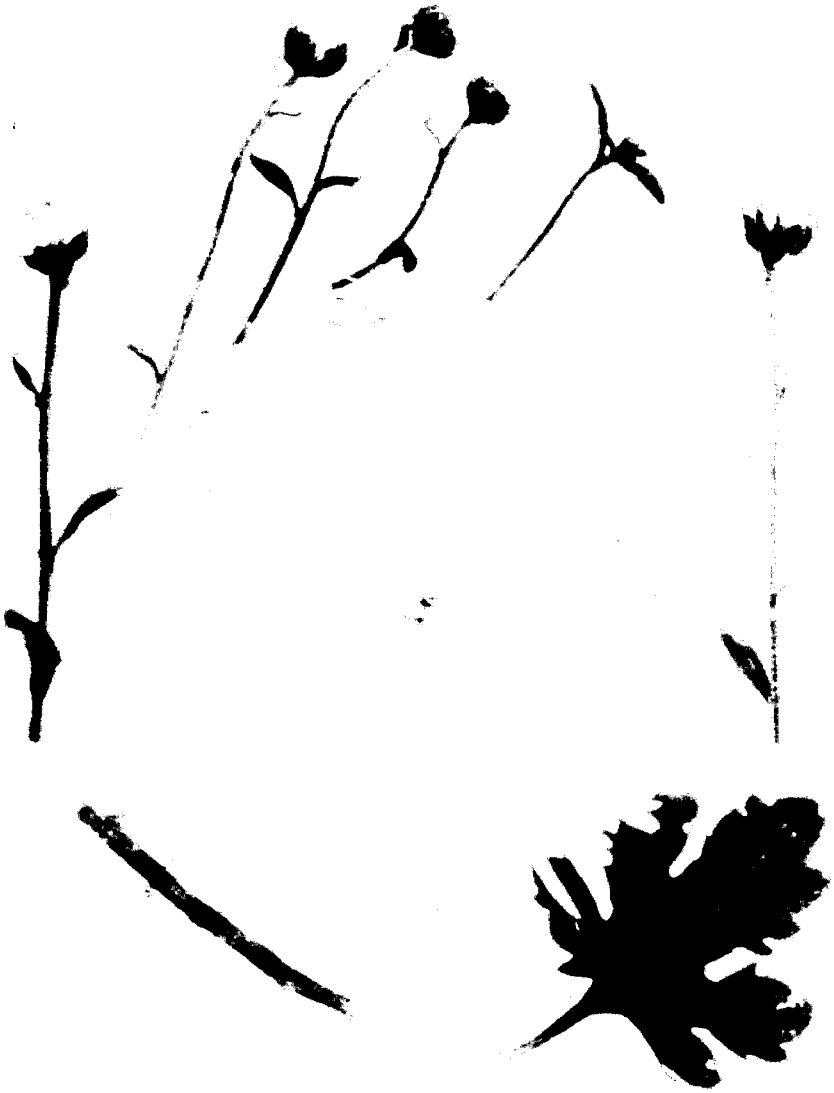
Inventor.
E. S. Boerner
By: Robb & Robb
Attorneys.

United States Patent Office

Plant Pat. 1,547
Patented Jan. 1, 1957

1,547

CHRYSANTHEMUM PLANT

Eugene S. Boerner, Newark, N. Y., assignor to Jackson & Perkins Company, Newark, N. Y., a corporation of New York Application February 27, 1956, Serial No. 568,128

1 Claim. (Cl. 47—60)

The present invention relates to a new and distinct variety of chrysanthemum plant of the decorative type, which was discovered by me as a sport of the variety named "Sea Gull" (Plant Patent No. 1130).

At the time of my initial discovery, plants of "Sea Gull" were being grown under my direction and supervision in the fields of my assignee at Newark, New York, and my attention was attracted to one particular plant by reason of the flowers borne thereby which appeared to be distinctly different in color from the usual color of the flowers of the "Sea Gull" variety. Upon closer examination, I found that one of the plants of "Sea Gull" had sported, and I thereupon promptly took steps to preserve the sport and to propagate the same for the purpose of producing additional plants from which more extensive observations and tests could be made. The subsequent observations and tests fully confirmed that the new sport generally resembled its parent "Sea Gull" in substantially all respects, except for the distinctly different Picric Yellow, overcast with Pinard Yellow, general color tonality of the flowers of the sport, and that these characteristics and distinctions come true to form and are established and transmissible through succeeding asexual propagations by top cuttings and by underground runners, as performed by me at Newark, New York.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Sport of "Sea Gull."

Classification: Decorative type.

Growth: Upright; clean; attains a height of from 2 to 2½ feet.

Cold resistance: Winter hardy in Northern New York, and does not burn.

Blooming period: In the Newark, New York, climatic area, blooming starts about August 25th and continues until severe freezing in October or November of the average season.

FLOWER (Observations made from specimens grown in a field at Newark, New York, in the early part of October, and in the early afternoon.)

Bud:

*Color.*—When sepals first divided—Pale Greenish Yellow, Plate 5. When petals begin to unfurl—Strontian Yellow, Plate 16. When half-blown: Inside of petals—Amber Yellow, Plate 16, overcast with Pale Lemon Yellow, Plate 4 at the tip end of the petal; outside of petals—Barium Yellow, Plate 16.

*Peduncle.*—Strong. Color—Light Cress Green, Plate 31.

Bloom:

*Size.*—From 4½ inches to 5 inches.

*Stem.*—Strong.

*Form.*—Decorative type, with pistils showing when center is fully open.

*Petalage.*—Very double.

*Color.*—Center of flower—Pinard Yellow, Plate 4. Outer petals—Martius Yellow, Plate 4. Base of petals—Light Dull Green-Yellow, Plate 17. Inside of petals—Picric Yellow, Plate 4, lightly overcast with Pinard Yellow, Plate 4. Reverse of petals—Naphthalene Yellow, Plate 16.

*Petals.*—Texture—medium. Form—long.

*Fragrance.*—Characteristic chrysanthemum.

PLANT

Form: Upright.

Growth: Vigorous; free.

Foliage:

*Size.*—Small.

*Quantity.*—Normal.

*Color.*—Upper side—Ivy Green, Plate 31; reverse side—Cress Green, Plate 31.

*Texture.*—Leathery.

I claim:

A new and distinct variety of chrysanthemum plant of the decorative type, substantially as herein shown and described, characterized particularly as to novelty by its general similarity to its parent variety "Sea Gull" (Plant Patent No. 1,130), but being distinguished therefrom by the Picric Yellow, overcast with Pinard Yellow, general color tonality of its flowers.

No references cited.